(12) United States Patent
Paltieli (10) Patent No.: US 6,200,279 B1
(45) Date of Patent: Mar. 13, 2001

(54) METHOD AND APPARATUS MONITORING THE PROGRESS OF LABOR

(75) Inventor: Yoav Paltieli, Haifa (IL)

(73) Assignee: Ultra-Guide Ltd., Haifa (IL)

( * ) Notice: Subject to any disclaimer, the term of this patent is extended or adjusted under 35 U.S.C. 154(b) by 0 days.

(21) Appl. No.: 09/072,850

(22) Filed: May 5, 1998

Related U.S. Application Data (60) Provisional application No. 60/045,556, filed on May 5, 1997.

(51) Int. Cl.⁷ .................................................... A61B 5/103
(52) U.S. Cl. ............................................ 600/588; 600/426
(58) Field of Search .................................. 600/304, 424, 600/425, 426, 427, 429, 587, 588, 591

(56) References Cited

U.S. PATENT DOCUMENTS

| | | |
|---|---|---|
| 3,768,459 | * 10/1973 | Cannon et al. . |
| 4,476,871 | 10/1984 | Hon . |
| 4,942,882 | 7/1990 | Bellinson . |
| 4,945,305 | 7/1990 | Blood . |
| 5,088,497 | 2/1992 | Ikeda . |
| 5,135,006 | 8/1992 | Bellinson . |
| 5,222,485 | 6/1993 | Jerath . |
| 5,406,961 | 4/1995 | Artal . |
| 5,438,996 | * 8/1995 | Kemper et al. . |
| 5,935,061 | * 8/1999 | Acker et al. ............................ 600/304 |

FOREIGN PATENT DOCUMENTS

| | | |
|---|---|---|
| 31 03 367 | * 8/1982 | (DE) . |
| 2158767 | * 6/1973 | (FR) . |

OTHER PUBLICATIONS

Keith P. Russell, M.D. "The Course & Conduct of Normal Labor & Delivery", Current Obstetric & Gynecologic Diagnosis & Treatment 4th Edition pp. 638,656–675.

* cited by examiner

Primary Examiner—Eric F. Winakur
(74) Attorney, Agent, or Firm—Kenyon & Kenyon (57) ABSTRACT

A method of monitoring the progress of labor in a mother during childbirth, by attaching a position sensor to a predetermined point on the mother's pelvic bones; monitoring the location of the position sensor in three-dimensional space relative to a reference; and monitoring the location of the fetal presenting part with respect to the predetermined point on the mother's pelvic bones. The location of the fetal presenting part may be indicated by a similar position sensor, or by imaging. Other conditions, such as effacement, cervical dilatation, and cervical position may also be monitored in a similar manner.

36 Claims, 8 Drawing Sheets

METHOD AND APPARATUS MONITORING THE PROGRESS OF LABOR

CROSS-REFERENCES TO RELATED APPLICATIONS

This patent application claims priority from U.S. Provisional Patent Application Ser. No. 60/045,556, filed on May 5, 1997.

FIELD AND BACKGROUND OF THE INVENTION

The present invention relates to a method and apparatus for monitoring the progress of labor during childbirth.

Normal labor is generally divided into three stages: The first stage begins with the onset of labor and ends when dilatation of the cervix is complete; the second stage begins at that point and ends with the complete birth of the baby; and this is followed by the third stage which ends with the delivery of the placenta. During labor it is common to use either an external ultrasonic system for recording the baby's heart rate, and an external system for detecting the mother's uterine contractions, or an electronic system to sense the baby's heart pulses by an electrode attached to the baby's head and the mother's contractions by a pressure catheter applied to the mother inside the uterus.

However, a number of other physiological conditions of the mother and baby during labor must also be monitored in order to determine the progress of labor. These additional conditions include: (1) effacement (the thinning out of the cervix that occurs before and during the first stage of labor); (2) cervical dilatation (the increase in size of the cervical opening); (3) position of the cervix (the relation of the cervix to the vaginal axis, normally the fetal head); and (4) station (the level of a predetermined point of the fetal presenting part with reference to the mother's pelvis). The more common determination of station is the distance between the tip of the fetal head and the ischial spines which can be palpable by the physician; but a more accurate determination of station is the distance between the bi-parietal diameter (BPD) of the fetal head and the mother's pelvic inlet.

The foregoing conditions are generally determined by a physical examination, i.e., by the insertion of a finger through the mother's vagina. However, the accuracy of such a "finger" examination is very subjective and depends to a great extent on the experience, judgment, and even finger size, of the physician. Other drawbacks in such a physical examination are that it can be done only at spaced intervals, it generally produces discomfort to the mother, and it involves a number of risks including contamination, infection, dislodgment of a fetal monitor, injury to the baby, etc. Failure to interpret the precise stage of the labor progress from the physical examination can result in injury or even death of the baby or of the mother.

Many devices have been proposed in the past for automatically monitoring these conditions. As examples, U.S. Pat. No. 4,476,871 proposes an elongated tube having electrodes spaced along its length to monitor cervical dilatation during labor; U.S. Pat. Nos. 4,942,882 and 5,135,006 propose a fetal monitor probe attached to the fetal head to monitor heart beat, which probe is calibrated to monitor progress of descent; U.S. Pat. No. 5,222,485 proposes an elongated inflatable sac to monitor the position of the fetus and the configuration of the cervix; and U.S. Pat. No. 5,406,961 proposes a pessary to monitor the configuration of the cervix. However, for one reason or another, none of the previously proposed devices has come into any widespread uses and the historical "finger" examination continues to be the one in common use to this day.

OBJECTS AND BRIEF SUMMARY OF THE INVENTION

An object of the present invention is to provide a method and apparatus having advantages over the conventional "finger" examination technique for monitoring the progress of labor in a mother during childbirth.

According to one aspect of the present invention, there is provided a method of monitoring the progress of labor in a mother during childbirth, comprising: attaching a position sensor to a predetermined point on the mother's pelvic bones; monitoring the location of the position sensor in three-dimensional space relative to a reference; and monitoring the location of the fetal presenting part with respect to the predetermined point on the mother's pelvic bones to provide an indication of the progress of labor.

Three embodiments of the invention are described below for purposes of example. In one embodiment, the location of the fetal presenting part, and also of the opposite sides of the end of the mother's uterine cervix, are monitored by position sensors attached to these respective elements. In a second described embodiment, the latter are monitored by operating an ultrasonic transducer to image the mother's cervix and pelvic bones, and the fetal head, on a screen, and by using a position sensor on the ultrasonic transducer, and a marker for marking the screen, to locate the positions of these elements. A third embodiment is described utilizing both the four position sensors applied to the mother and the fetal presenting part, and a fifth position sensor applied to an ultrasonic transducer for imaging and locating the mother's cervix and pelvic bones and the fetal head According to further features in the described first and third embodiments, the cervical dilatation of the mother's cervix is continuously indicated by continuously monitoring the positions of the position sensors applied to the opposite sides of the end of the cervix, and continuously displaying the spatial distance between them. The position of the fetal presenting part (e.g., fetal head) is also continuously indicated by continuously monitoring and displaying their respective locations According to further features in the described preferred embodiments, the above conditions are computed and displayed in the form of units of distance (e.g., cm), and/or in the form of a graph, called a Partogram, showing the interrelation of the cervical dilatation and the descent of the fetal presenting part According to a further aspect of the invention there is provided apparatus for monitoring the progress of labor in a mother during childbirth, comprising: a position sensor for attachment to a predetermined point on the mother's pelvic bones, and for producing an output signal identifying its location in space; means for sensing the location of the fetal presenting part with respect to the predetermined point on the mother's pelvic bones, and for producing an output signal identifying the location of the fetal presenting part; a computer connected to receive the output signals; and an output device controlled by the computer for outputting the position of the fetal presenting part with respect to the predetermined point of the mother's pelvic bones The output device is preferably a display, but could be a plotter, recorder, or other device for displaying, recording, and/or processing the data outputted by the computer As will be described more particularly below, such a method and apparatus permits the progress of labor to be monitored in a manner which is continuous rather than intermittent, which is less dependent for accuracy on the experience, judgment or finger size of the attendant in the conventional "finger examination", which subjects the mother to less discomfort, and which involves less risk of contamination, infection, dislodgment of a fetal monitor, or injury to or death of the baby or mother due to a wrong assessment of the fetal position or of labor progress. Moreover, this technique enables more precise monitoring of the critical condition, namely the changes in the spatial distance of the BPD of the baby's head with respect to the pelvic inlet Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
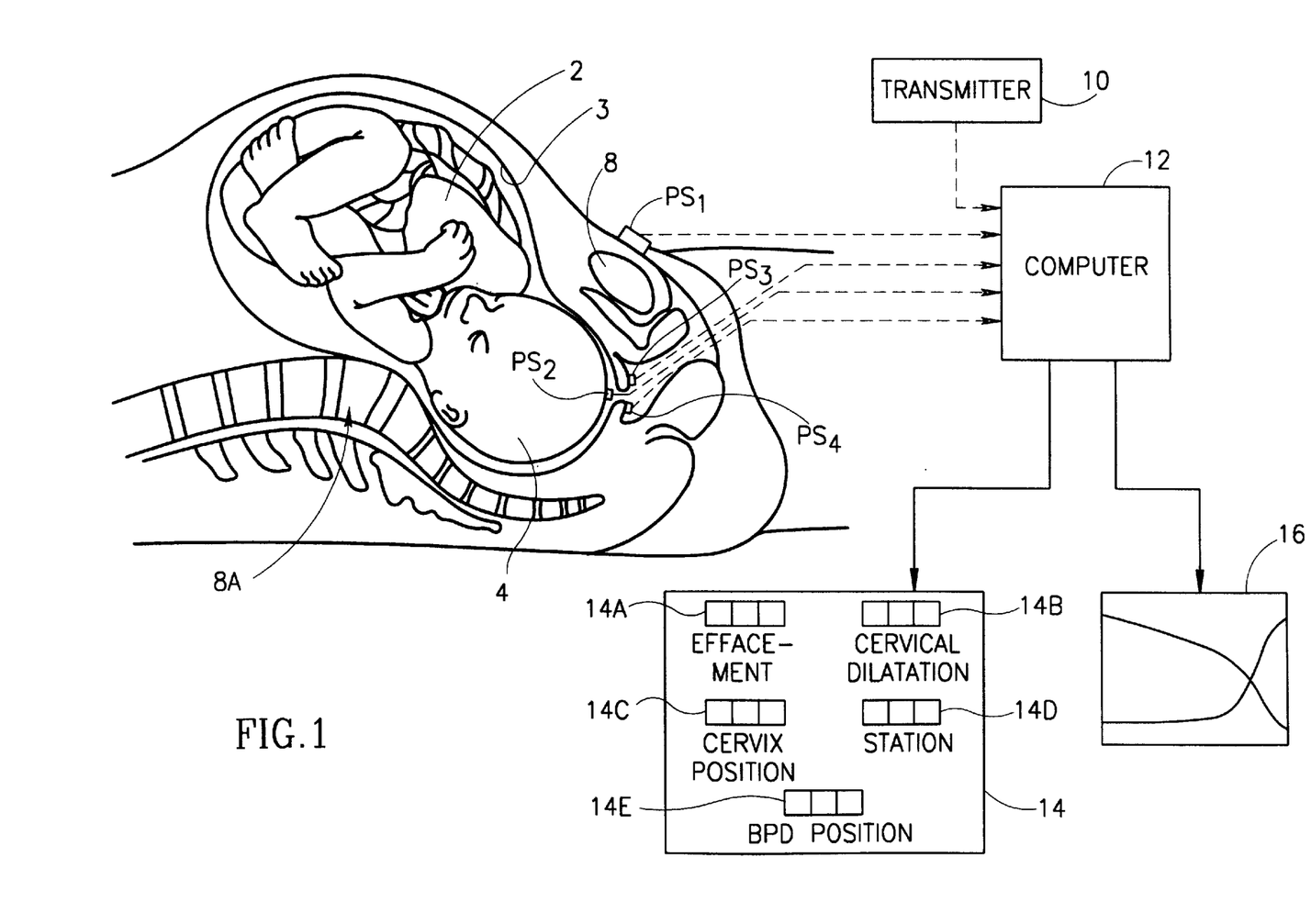
FIG. 1 is a block diagram illustrating one form of system constructed in accordance with the present invention.
Figure 2:
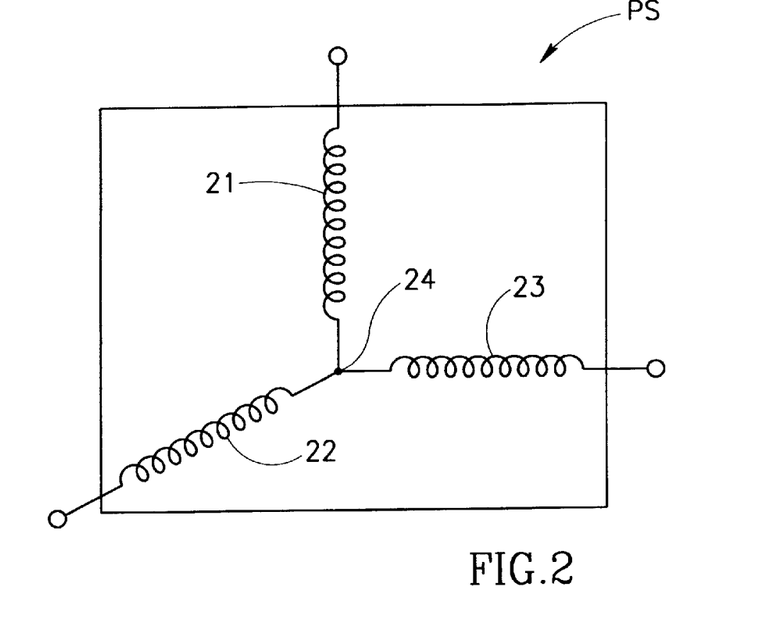
FIG. 2 illustrates one of the position sensors in the system of FIG. 1.
Figure 3:
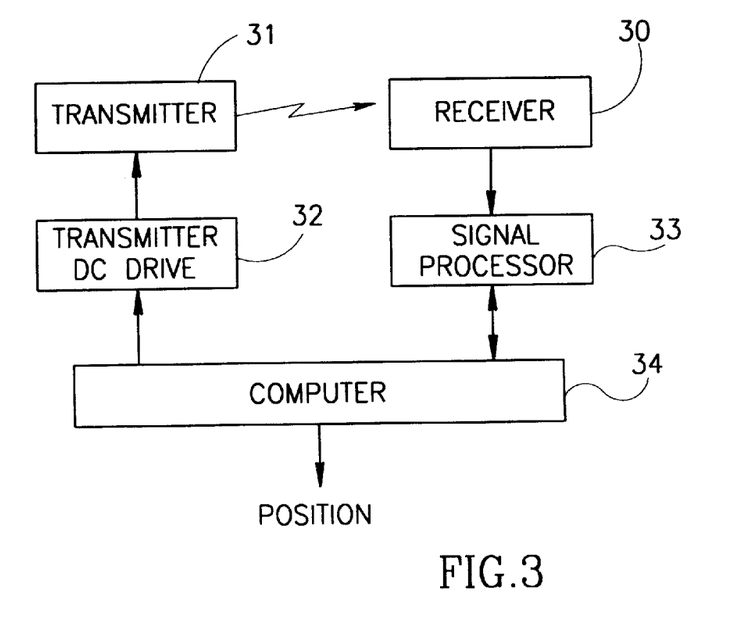
FIG. 3 is a block diagram of one type of position sensor system that may be used.
Figure 4:
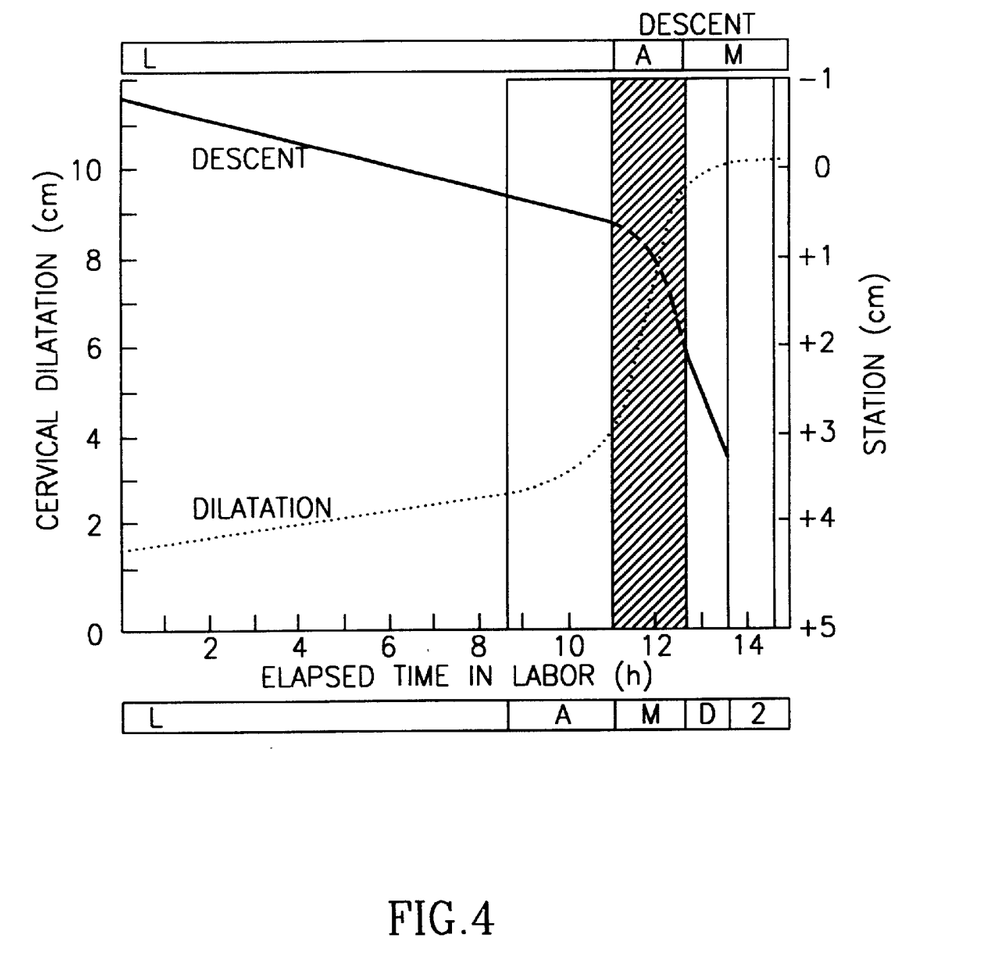
FIG. 4 more particularly illustrates the Partogram display in the system of FIG. 1.

FIG. 1 schematically illustrates the mother's womb particularly illustrated in FIG. 4, is of special value since it provides a visual display of the progress of labor and can be recorded if desired. By using the Partogram, a better determination can be made whether labor is progressing normally. "Alert" and "action" lines may be printed on the Partogram to provide a visible indication of whether labor is progressing normally or abnormally, and thereby to better alert the attending personnel to take prompt action if necessary. Such an "electronic Partogram" can also markedly reduce the number of prolonged labors, the rate of intrapartum, post partum and early neonatal infections, the number of unnecessary interventions, and neonatal trauma due to wrong assessment of the fetal head.

Figure 5:
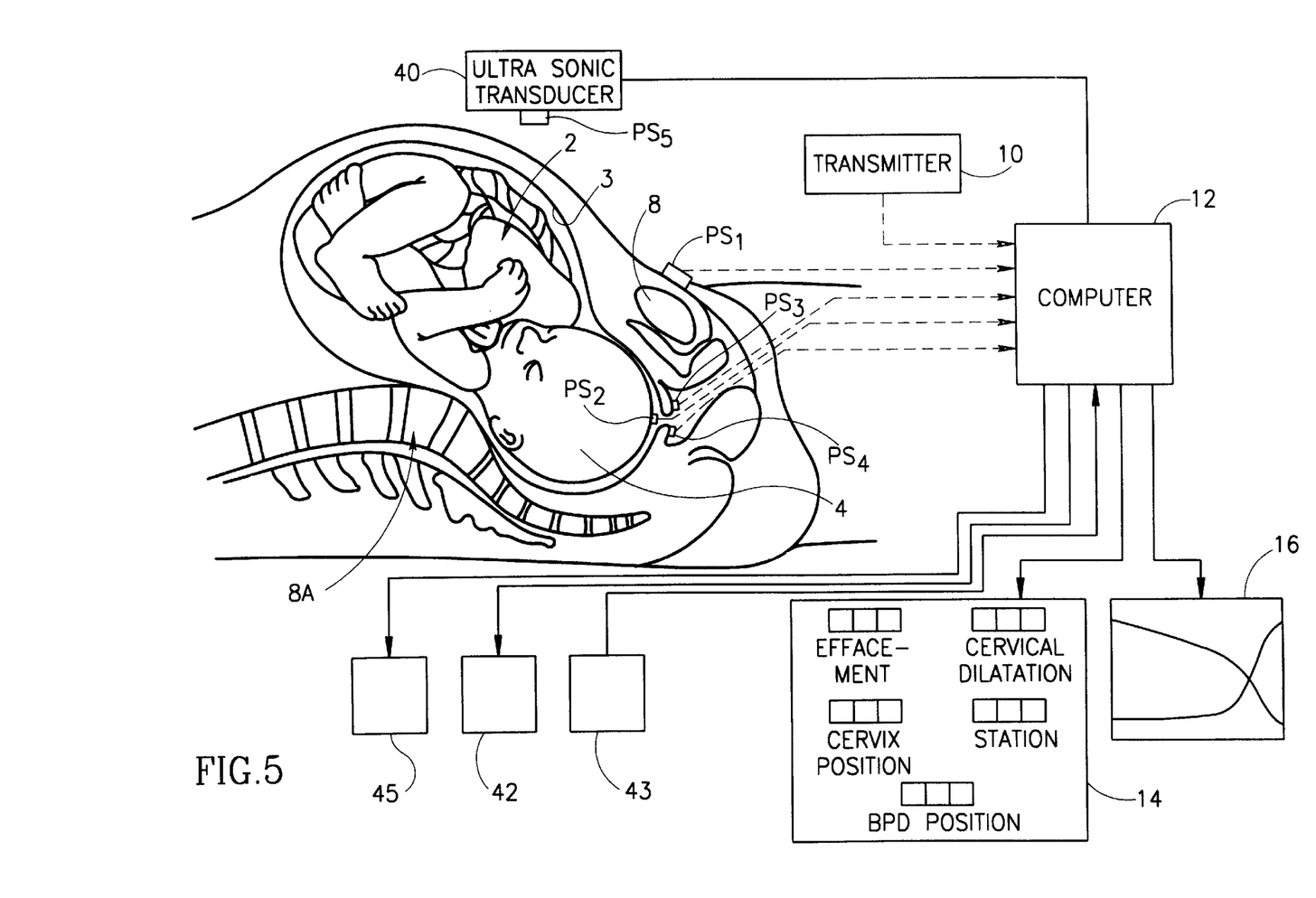
FIG. 5 is a block diagram illustrating an imaging system for displaying the image of the mother's womb, particularly the cervix, pelvic bones, and the fetal head to better show the progress of the labor.
Figure 6A:
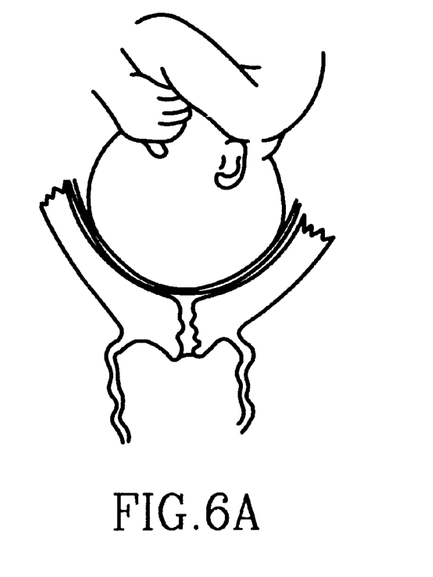
FIGS. 6A–6D illustrate typical displays produced by the system of FIG. 5 during the various stages of labor.
Figure 6B:
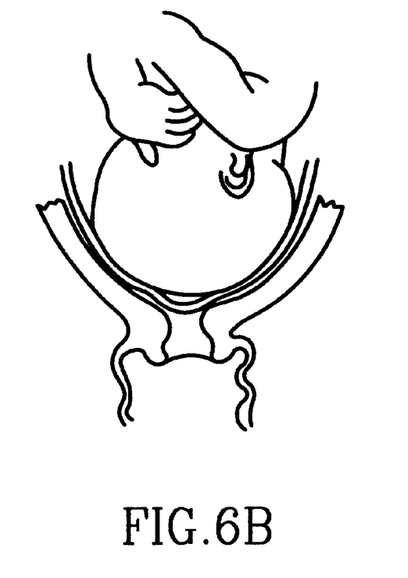
Figure 6C:
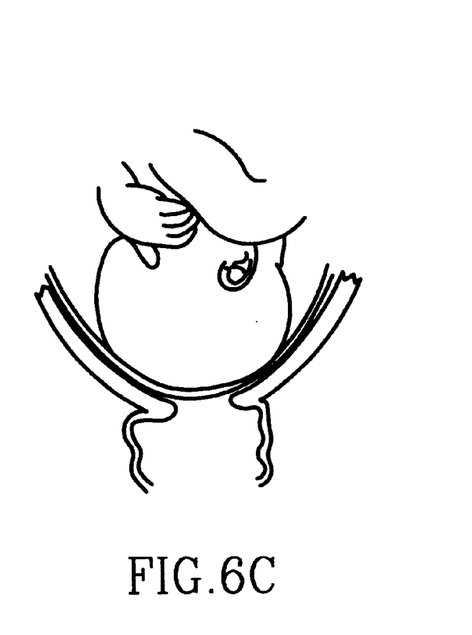
Figure 6D:
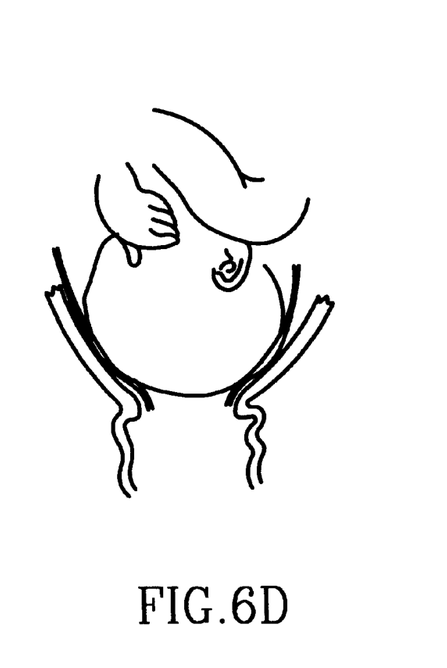

FIG. 5 illustrates a monitoring system similar to that of FIG. 1 but further equipped with an imaging system for imaging the womb area of the mother and for continuously displaying the mother's cervix, pelvic bones, and fetal head (or other presenting part).

Thus, FIG. 5 includes an ultrasonic transducer 40 for imaging the womb area, via the computer 12, on an image display 42. It also includes a position sensor PS5 attached to the ultrasonic transducer 40. Thus, any point in the image on display 42 may be selected by a marker device 43, such as a mouse or touch screen, and its location fed into the computer 12 to identify the location of the respective point with respect to the location of position sensor PS1 attached to the mother's pubic bones. With this information, the computer 12 can compute the various relationships displayed in displays 14 and 16, thereby obviating the need for the positions sensors PS2, PS3 and PS4. The image displayed in display 42 may be used in the same manner for marking the BPD on the fetal head as illustrated in FIG. 8, thereby enabling particularly the spatial distance between the fetal BPD and the pelvic inlet to be computed and monitored.

It will be appreciated that other reference points, other than the BPD or the tip of the fetus head, as well as any other point of the mother's pelvis, may be used as the reference points for monitoring the progress of the labor. This freedom is important because of the variety of preferences among various physicians.

Figure 7:
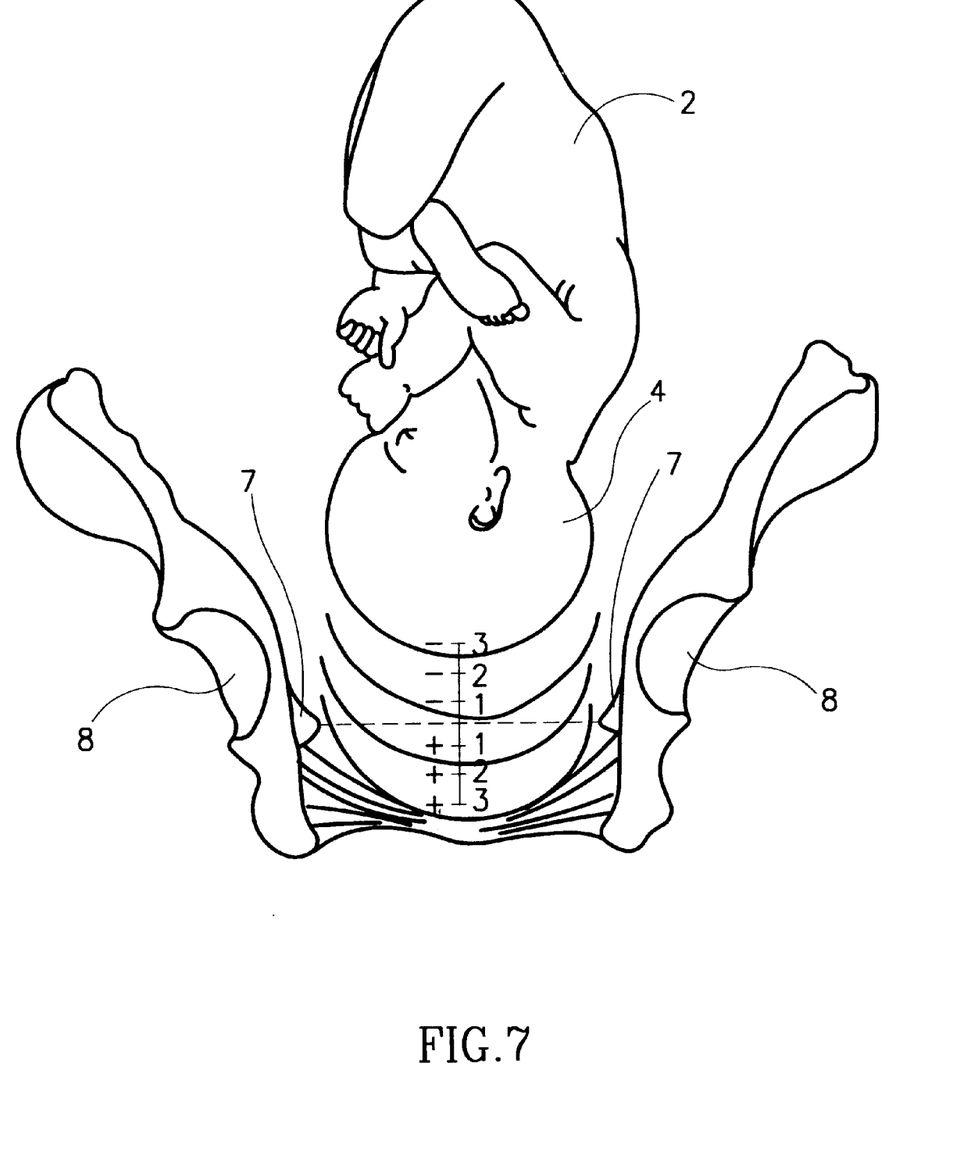
FIG. 7 illustrates a typical display produced by the system of FIG. 5 during the descent of the fetal head.
Figure 8:
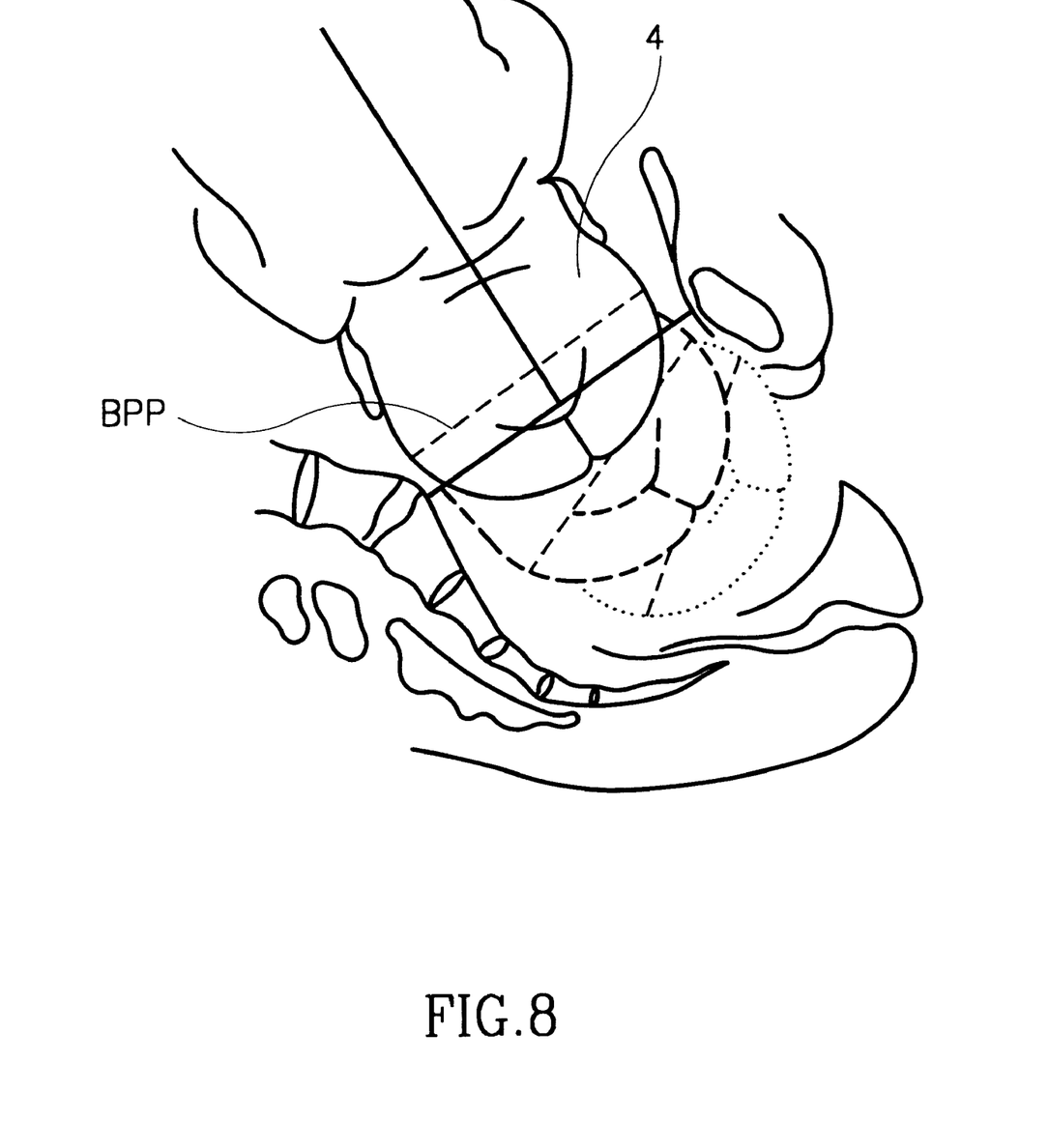
FIG. 8 illustrates how the monitored data may be processed to display the changes in the spatial distance of the BPD of the baby's head with respect to the mother's pelvic inlet.

The imaging system illustrated in FIG. 5 could also be used to provide a visual image of the various stages of labor, e.g., as illustrated in FIGS. 6A–6D showing the progressive dilatation and effacement of the cervix, or as illustrated in FIGS. 7 and 8 showing the progressive descent of the fetal head tip through the various stations with respect to the ischial spines 7 (FIG. 7) or mother's pelvic inlet (FIG. 8).

If the imaging system is used together with all five position sensors PS1–PS5 illustrated in FIG. 5, the ultrasound imaging may be used only to measure the BPD at the beginning of labor or later. The computer then determines the distance between the BPD and the tip of the fetal head, and thereafter it can use the position of the tip of the fetal head also to determine the BPD position. The ultrasound imaging may thereafter be used only for verification if desired. It can also be used to verify cervical dilatation and effacement.

If the system illustrated in FIG. 5 is used with only the ultrasound imaging and position sensors PS1 and PS5, the monitoring would preferably not be continuous but only intermittent, i.e., only when it is desired to monitor a specific stage in the progress of the labor.

Figure 9:
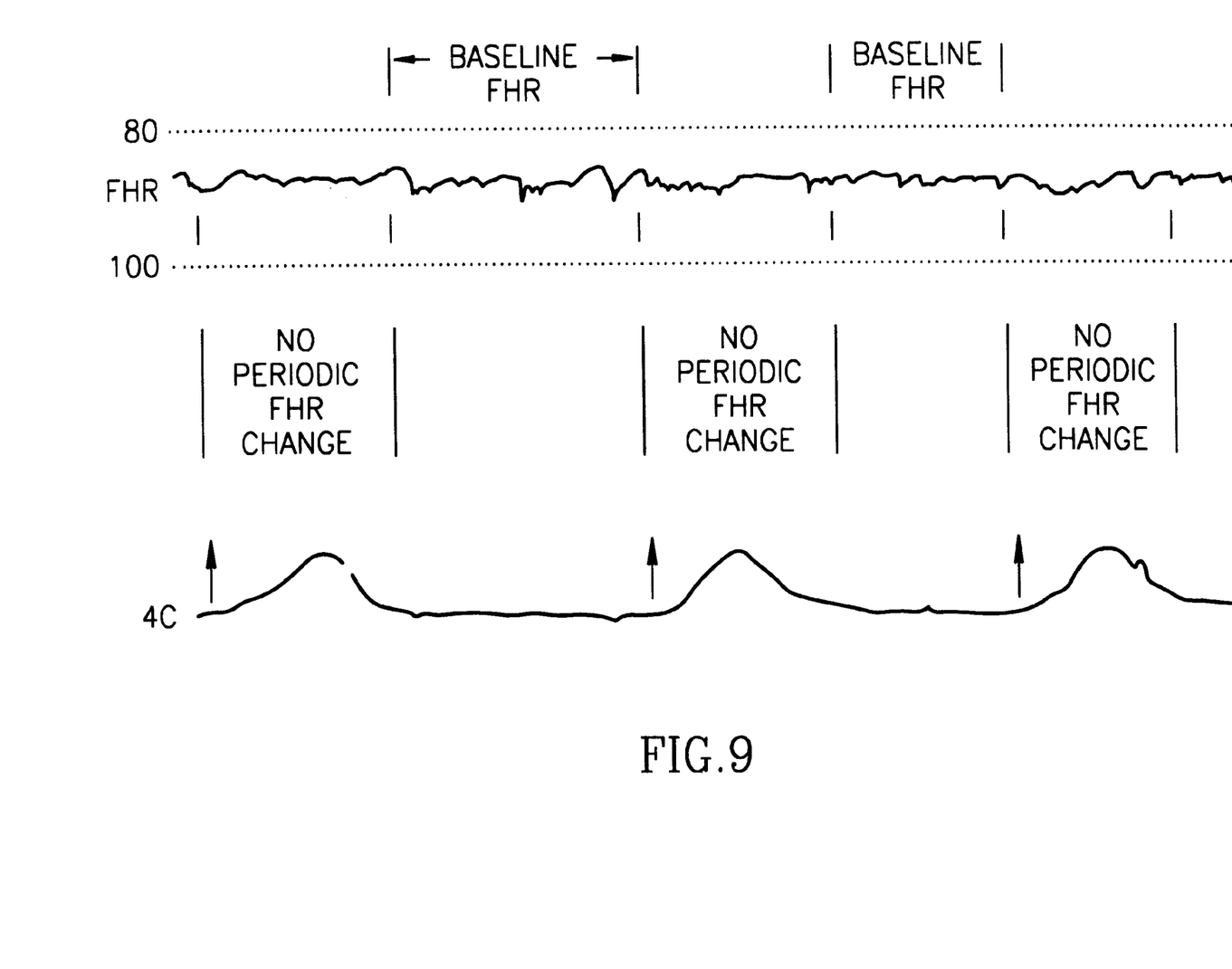
FIG. 9 illustrates a fetal heart monitoring display and uterine contractions that may be included in the above-described systems of FIG. 1 or FIG. 5.

The system illustrated in FIG. 5 may also be used for sensing contractions in the mother's uterus. Thus, during contractions, the fetal head moves slightly, and the dilatation also grows slightly; and after contractions, they both retract to their previous positions. By thus observing the dilatation and/or fetal head position as a function of time, the attending physician may discern the occurrence of contractions as well as the duration and strength of such contractions. In addition, by including a heart pulse sensor in the fetal head position sensor PS2, the physician may observe the relation of the fetal heart rate (FHR) in relation to the uterine contractions (UC), to show the relationship between the two as illustrated in FIG. 9. Computer 12 may be programmed to receive the above information from the various sensors and produce, in a monitor 45, a display corresponding to the fetal heart rate (FHR) in relation to the uterine contractions (UC), as illustrated in FIG. 9. Such information is particularly desirable if the presence of complications is established or anticipated.

While separate displays are shown in the drawings, it will be appreciated that these displays could be in the form of windows on the same large computer display.

While the invention has been described with respect to several preferred embodiment, it will be appreciated that these are set forth merely for purposes of example, and that many other variations, modifications and applications of the invention may be made.

What is claimed is:

1. A method of monitoring a progress of labor in a mother during childbirth, comprising:
    attaching a first position sensor to a predetermined point on the mother's pelvic bone;
    monitoring a location of said first position sensor in three-dimensional space relative to a reference location, and
    monitoring the location of a fetal presenting part with respect to said predetermined point on pelvic bones of the mother to provide an indication of the progress of labor.

2. The method according to claim 1, further comprising monitoring the location of the opposite sides of an end of the mother's uterine cervix with reference to each other to provide an indication of a dilatation of the mother's cervix.

3. The method according to claim 2, further comprising monitoring the location of the opposite sides of said end of the mother's uterine cervix with reference to the fetal presenting part and the mother's pelvic bones to provide an indication of the cervical position of the mother.

4. The method according to claim 2, wherein the location of said fetal presenting part is monitored by attaching a second position sensor to an outer tip of said fetal presenting part and monitoring the location of said second position sensor.

5. The method according to the claim 4, wherein the locations of said opposite sides of the mother's uterine cervix are monitored by attaching third and fourth position sensors to them, and monitoring their respective locations.

6. The method according to claim 5, wherein the station of the fetal presenting part is continuously indicated by continuously monitoring the positions of said first and second position sensors, and continuously displaying the spatial distance between them.

7. The method according to claim 6, wherein the cervical dilatation of the mother's cervix is continuously indicated by continuously monitoring the positions of said third and fourth position sensors and continuously displaying the spatial distance between them.

8. The method according to claim 7, wherein said cervical dilatation and said station are computed and displayed in centimeters.

9. The method according to claim 7, wherein said cervical dilatation and said station are computed and displayed in the form of a Partogram showing the interrelation of the cervical dilation and the descent of the fetal presenting part.

10. The method according to claim 5, wherein effacement of the mother's cervix is continuously indicated by continuously monitoring and displaying the spatial distance of said second position sensor from said third and fourth position sensors.

11. The method according to claim 5, wherein the effacement and position of the mother's cervix is continuously indicated by continuously monitoring and displaying the spatial distances between said first, second, third and fourth position sensors.

12. The method according to claim 11, wherein said effacement and position of the mother's cervix are computed and displayed in centimeters.

13. The method according to claim 5, wherein the position of the mother's cervix is continuously indicated by continuously monitoring and displaying the angle of the cervical axis as indicated by said second, third and fourth position sensors.

14. The method according to claim 5, wherein contractions in the mother's uterine cervix are sensed, and the fetal heart rate is sensed and is displayed in relation to the uterine contractions.

15. The method according to claim 14, wherein said contractions in the mother's uterine cervix are sensed by monitoring said second, third and fourth position sensors to indicate the variations in the position of the fetal presenting part and of the cervix.

16. The method according to claim 1, wherein the location of said fetal presenting part is monitored by attaching a second position sensor to an ultrasonic transducer, operating said ultrasonic transducer to image said fetal presenting part on a screen, monitoring the location of said second position sensor and thereby the location of said ultrasonic transducer to which it is attached, and determining the location of the fetal presenting part as imaged on said screen.

17. The method according to claim 16, wherein the monitored locations of said first position sensor and of the fetal presenting part are processed to provide an indication of the spatial distance of the bi-parietal diameter (BPD) of the fetal head with respect to the mother's pelvic inlet.

18. The method according to claim 1, wherein, before attaching said first position sensor to a predetermined point on the mother's pelvic bones and monitoring its location, the entire spatial position of the mother's pelvis is analyzed.

19. The method according to claim 18, wherein the mother's pelvis is analyzed by:
    attaching a position sensor to one known point of the pelvis and outputting an electrical signal identifying the location of said one point;
    attaching the position sensor to a second known point of the pelvis and outputting an electrical signal identifying the location of said second point;
    attaching said position sensor to a third known point of the pelvis and outputting an electrical signal identifying the location of said third point; and
    processing said first, second, third electrical signals to compute an entire spatial position of the pelvis.

20. The method according to claim 19, wherein said first point is a left anterior superior spine; said second point is a central point of the symphys pubis; and said third point is a right anterior superior spine.

21. The method according to claim 20, wherein, after the entire spatial position of the pelvis is mapped, said position sensor at said third point is left attached to said third point while its location is monitored during the mother's labor.

22. An apparatus for monitoring a progress of labor, comprising:
    at least one first position sensor provided for an attachment to a predetermined point on the mother's pelvic bones, and producing a first output signal identifying its location in space;
    means for sensing a location of a fetal presenting part with respect to said predetermined point on the mother's pelvic bones, and producing a second output signal identifying the location of said fetal presenting part;
    a computer in operative communication with said at least one first position sensor and said sensing means to receive said first and second output signals corresponding to the position of said at least one first position sensor and said location of said fetal presenting part; and an output device controlled by said computer for outputting the position of said fetal presenting part with respect to said predetermined point of the mother's pelvic bones.

23. The apparatus according to claim 22, further comprising means for sensing the locations of opposite sides of the mother's uterine cervix with reference to each other to produce output signals which are received by said computer and processed to control said output device for outputting an indication of the dilatation of the mother's cervix.

24. The apparatus according to claim 23, further comprising means for sensing the locations of the opposite sides of the mother's uterine cervix with reference to the fetal presenting part and the mother's pelvic bones to produce output signals which are received by said computer and processed to control said output device for outputting an indication of the cervical position of the mother.

25. The apparatus according to claim 23, wherein said means for sensing the location of the fetal presenting part with reference to said predetermined point of the mother's pelvic bones comprises a second position sensor for attachment to the outer tip of the fetal head for producing an output signal to the computer identifying the location of said second position sensor.

26. The apparatus according to claim 25, wherein said means for sensing the locations of the opposite sides of the mother's uterine cervix include third and fourth position sensors for attachment to the opposite sides of the mother's uterine cervix and for producing output signals to the computer identifying their respective locations.

27. The apparatus according to claim 26, wherein said computer computes, and said output device displays, the station of the fetal presenting part as the spatial distance between said first and second position sensors.

28. The apparatus according to claim 27, wherein said computer computes, and said output device displays, the cervical dilatation of the woman's cervix as the spatial distance between said third and fourth position sensors.

29. The apparatus according to claim 28, wherein said computer computes, and said output device displays, said cervical dilation and said station in centimeters.

30. The apparatus according to claim 28, wherein said computer computes, and said output device displays, said cervical dilatation and said station in the form of a Partogram showing the interrelation of the cervical dilatation and the descent of the fetal presenting part.

31. The apparatus according to claim 26, wherein said computer computes, and said output device displays, the effacement of the mother's cavity as the spatial distance of said second position sensor from said third and fourth position sensors.

32. The apparatus according to claim 26, wherein said computer computes, and said output device displays, the position of the mother's cervix as the spatial distances between said first, second, third and fourth position sensors.

33. The apparatus according to claim 32, wherein said effacement and position of the mother's cervix are computed and displayed in centimeters.

34. The apparatus according to claim 26, wherein said computer computes, and said output device displays, the angle of the cervical axis as indicated by said second, third and fourth position sensors.

35. The apparatus according to claim 23, wherein said means for sensing the locations of the fetal presenting part and of the opposite sides of the mother's uterine cervix comprises:

an ultrasonic transducer to image said fetal presenting part and uterine cervix on screen;

a position sensor attached to said ultrasonic transducer for producing at least one further output signal identifying its location to the computer; and a marker for marking at least one selected point of the fetal presenting part, and the opposite sides of the mother's uterine cervix, in an image produced on the screen by said ultrasonic transducer, and for outputting electrical signals identifying their respective locations on the computer.

36. The apparatus according to claim 35, wherein said marker is adapted to mark the bi-parietal diameter (BPD) of the fetal head as imaged on the screen, whereby said computer computes the distances between said BPD and the mother's pelvic inlet.

* * * * *